(12) United States Patent
Lux et al.

(10) Patent No.: US 9,693,704 B2
(45) Date of Patent: Jul. 4, 2017

(54) RMS ELECTROCARDIOGRAPHY SYSTEM AND METHOD

(71) Applicants: COVANCE INC., Princeton, NJ (US); COVANCE CENTRAL DIAGNOSTICS INC., Reno, NV (US)

(72) Inventors: Robert L. Lux, Park City, UT (US); Jay W. Mason, Reno, NV (US)

( * ) Notice: Subject to any disclaimer, the term of this patent is extended or adjusted under 35 U.S.C. 154(b) by 0 days.

(21) Appl. No.: 14/467,825

(22) Filed: Aug. 25, 2014

(65) Prior Publication Data
US 2014/0364754 A1 Dec. 11, 2014

Related U.S. Application Data

(62) Division of application No. 11/484,539, filed on Jul. 11, 2006, now Pat. No. 8,849,381.

(51) Int. Cl.
*A61B 5/0452* (2006.01)
*A61B 5/0408* (2006.01)
*A61B 5/00* (2006.01)

(52) U.S. Cl.
CPC ......... *A61B 5/0452* (2013.01); *A61B 5/0408* (2013.01); *A61B 5/7275* (2013.01)

(58) Field of Classification Search
CPC ..... A61B 5/0452; A61B 5/046; A61B 5/0464; A61B 5/0468; A61B 5/0472; A61B 5/048
USPC ........................................ 600/509, 517–528
See application file for complete search history.

(56) References Cited

U.S. PATENT DOCUMENTS

| | | | |
|---|---|---|---|
| 5,560,370 A * | 10/1996 | Verrier et al. ............... | 600/518 |
| 5,792,065 A | 8/1998 | Xue et al. | |
| 5,954,664 A | 9/1999 | Seegobin | |
| 2006/0264769 A1 * | 11/2006 | Satin et al. ................... | 600/509 |

FOREIGN PATENT DOCUMENTS

JP            11318842        11/1999

OTHER PUBLICATIONS

Fuller, et al., "Estimates of Repolarization Dispersion From Electrocardiographic measurements", Circulation 102, Mar. 16, 2000, pp. 685-691.*

Fuller, et al., "Estimates of Repolarization Dispersion From Electrocardiographic Measurements", Circulation 102, Mar. 16, 2000, pp. 685-691.

Fuller, et al., "Estimates of Repolarization and Its Dispersion From Electrocardiographic Measurements: Direct Epicardial Assesment in the Canine Heart", Journal of Electrocardiology. vol. 33, No. 2, Apr. 2000, pp. 171-180.

(Continued)

*Primary Examiner* — Christopher D Koharski
*Assistant Examiner* — Roland Dinga

(57) ABSTRACT

A system for assessing a cardiac condition of a subject includes a sensor configured to record a plurality N of electrocardiographic signals from the subject to generate an ECG (electrocardiogram). The system further includes a processor configured to compute an RMS (root-mean-square) magnitude function from the recorded signals, and to measure from the RMS magnitude function an RMS variable that contains information about the cardiac condition of the subject. The ECG may be a standard 12-lead clinical ECG. The measured RMS variables may include RMS T-wave width, RMS RT recovery time, and RMS QT interval.

7 Claims, 14 Drawing Sheets

(56) References Cited

OTHER PUBLICATIONS

Compton SJ, Lux RL, Ramsey MR, Strelich KR, Sanguinetti MC, Green LS, Keating MT, and Mason JW: Genetically defined therapy of inherited long-QT syndrome. Correction of abnormal repolarization by potassium [see comments], Circulation 94: 1018-22, 1996.

Lux RL, Fuller MS, MacLeod RS, Ershler PR, Punske BB, and Taccardi B: Noninvasive indices of repolarization and its dispersion. J Electrocardiol 32:153-7, 1999.

Lux RL, Hilbel T, Brockmeier K: Electrocardiographic measures of repolarization revisited: Why? What? How?, J Electrocardiol 34:259-264, 2001.

* cited by examiner

Fig. 2A  1 Beat 12 Lead ECG

| Rx | HR | QTcF | RMS-TW | P value (columns 4 & 5) |
|---|---|---|---|---|
| Day 2 | -10 | 15 | 30 | =.01 |
| Day 3 | -15 | 20 | 50 | =.001 |
| 2 vs 3 | 5 | 5 | 20 | <.0001 |
| P value (rows 2&3) | =.01 | =.04 | <.0001 | |

FIG. 3A

| Linear Regression Slopes: TW and QT Interval vs Heart Rate |||||||
|------|--------|--------|-------|-------|-------|-------|
|      | TW d0  | TW d1  | TW d2 | QT d0 | QT d1 | QT d2 |
| min  | -0.058 | -0.099 | -0.18 | 0.092 | 0.123 | 0.052 |
| max  | 0.054  | 0.075  | 0.095 | 0.203 | 0.279 | 0.311 |
| mean | 0.013  | 0.017  | 0.005 | 0.129 | 0.195 | 0.188 |
| sd   | 0.033  | 0.043  | 0.077 | 0.038 | 0.052 | 0.066 |

FIG. 3B

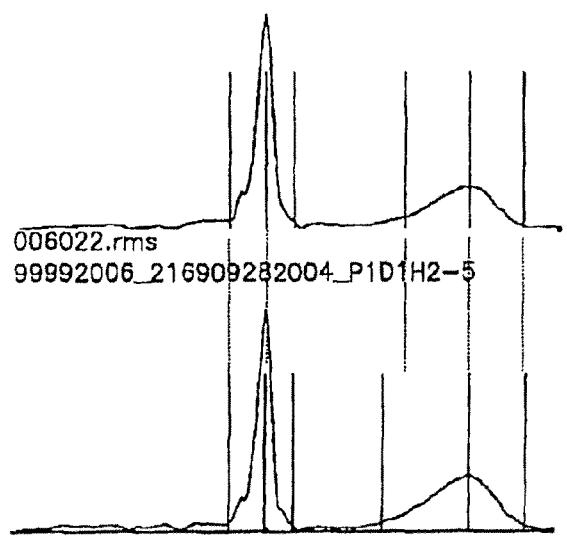
CL 763   FIG. 7A
CL 734   FIG. 7B

RMS ELECTROCARDIOGRAPHY SYSTEM AND METHOD

This application is a Divisional of application Ser. No. 11/484539, filed Jul. 11, 2006, title RMS ELECTROCARDIOGRAPHY SYSTEM AND METHOD the disclosure of which is incorporated herein by reference in its entirety.

BACKGROUND

Cardiac electrophysiologic measurements may provide useful diagnostic information. As one example, ventricular repolarization may be an indicator of arrhythmogenic risk. Ventricular repolarization may be visualized clinically in the electrocardiographic T wave, but T wave morphology is highly volatile because it is influenced by factors such as heart rate, autonomic nerve tone, pharmacological interventions, and electrolyte imbalances. Factors such as slow conduction, conduction block, spatially heterogeneous repolarization, and rate dependent changes in both conduction and repolarization may also contribute to complex electrophysiologic conditions that may increase the chances of life threatening cardiac arrhythmias.

To assess repolarization change, the QT interval, the time between the onset of the ECG (electrocardiogram) QRS complex and the end of the ECG T wave may be measured. Measurement of the QT interval may entail a number of difficulties, however. For example, T offset occurs during a low signal-to-noise (SNR) portion of the ECG, and may depend upon the leads in which the QT interval is measured as well as upon the activation sequence.

Accordingly, there is a need for more reliable systems and methods for assessing cardiac electrophysiologic phenomena such as ventricular repolarization.

SUMMARY

A system for assessing cardiac condition of a subject may include a sensor configured to record a plurality N of electrocardiographic signals from the subject to generate an ECG (electrocardiogram). The system may further include a processor configured to compute an RMS (root-mean-square) magnitude function from the recorded signals, and to measure from the RMS magnitude function one or more variables that contain information about the cardiac condition of the subject.

A method of assessing cardiac condition of a subject may include recording a plurality of electrocardiographic signals of the subject, and deriving an RMS magnitude function from the plurality of recorded signals. The method may further include measuring from the RMS magnitude function RMS variables that contain information about the cardiac condition.

BRIEF DESCRIPTION OF THE DRAWINGS

FIG. 2A illustrates the superimposed signals from the 12-leads of a standard clinical ECG.

FIG. 3A is a table displaying the percent change in ECG intervals measured on 12-lead ECGs in a group of subjects that received sotalol. FIG. 3B is a table from the same study showing the linear regression of QT and RMS-TW on the RR interval.

FIGS. 7A and 7B illustrate RMS signals in a subject who received sotalol that show changes in TW.

DETAILED DESCRIPTION

In the present disclosure, systems and methods are described in which an RMS magnitude function of a multi-lead electrocardiogram is used to measure times and intervals relevant for cardiac electrophysiologic evaluations. The RMS measurements described below allow RMS variables to be estimated. These RMS variables may include, but are not limited to: mean time of ventricular depolarization (time of RMS R peak), mean time of ventricular repolarization (time of RMS T peak), mean action potential duration (the interval between RMS R and T peaks, i.e. the RT interval or RTI), and dispersion of action potential downstroke times (RMS T width or TW). The RMS magnitude function may be computed from ECGs recorded from a few unipolar or bipolar leads as used in long term (Holter) monitoring, or from standard 12-lead ECGs, or from ECGs recorded from hundreds of leads used in cardiac mapping.

Figure 1:
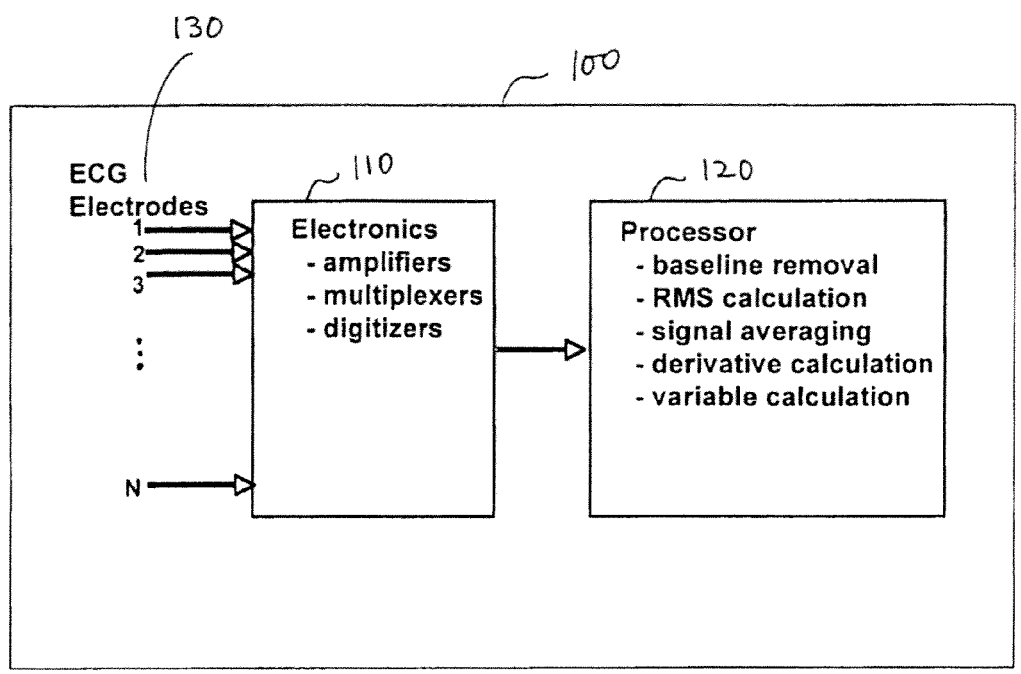
FIG. 1 is a schematic block diagram of a system for assessing cardiac condition of a subject, in accordance with one embodiment of the present disclosure.

FIG. 1 is a schematic block diagram of a system 100 for assessing a cardiac condition of a subject, in accordance with one embodiment of the present disclosure. In overview, the system 100 includes electronics 110 for amplifying, filtering, sampling, digitizing, and storing a plurality of N electrocardiographic signals from the subject to generate an ECG (electrocardiogram); and a processor 120 configured to process the electrocardiographic signals recorded by the electronics 110. In particular, the processor 120 is configured to compute an RMS (root-mean-square) magnitude function from the recorded electrocardiographic signals, and to measure from the RMS magnitude function an RMS variable that contains information about the cardiac condition of the subject. The system 100 may include a plurality N of monitoring electrodes 130 configured to receive the electrocardiographic signals from the subject when coupled to the subject.

As described in detail below, many different variables may be measured from the RMS ECG using the methods and systems of the present disclosure. These variables may include, but are not limited to the times of QRS onset, R peak, T onset, T peak and T offset. From these variables, one can calculate the RMS R peak to T peak interval (RTI), an estimate of the mean ventricular action potential duration; the RMS T-wave width (TW), an estimate of dispersion of ventricular repolarization times; the RMS QT interval (QT), the RMS ECG equivalent of the standard QT interval; the mean ventricular activation time (AT); and the mean ventricular repolarization time (RT).

Figure 2B:
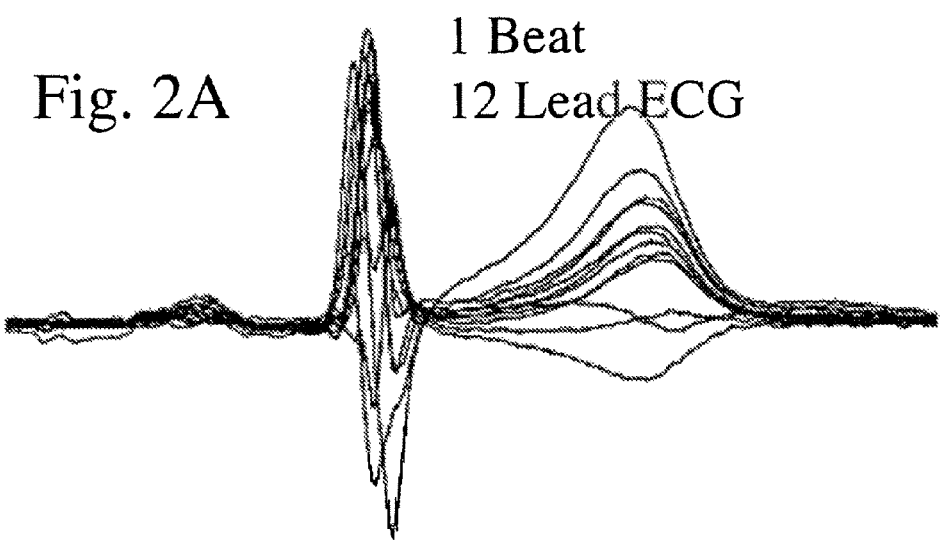
FIG. 2B illustrates an RMS ECG magnitude function derived in accordance with one embodiment of the present disclosure, including fiducial marks delineating estimates of the mean ventricular activation time (AT), the mean ventricular recovery time (RT), the T-wave width (TW), the mean ventricular repolarization interval (RTI), and the QT interval.
Figure 2B:
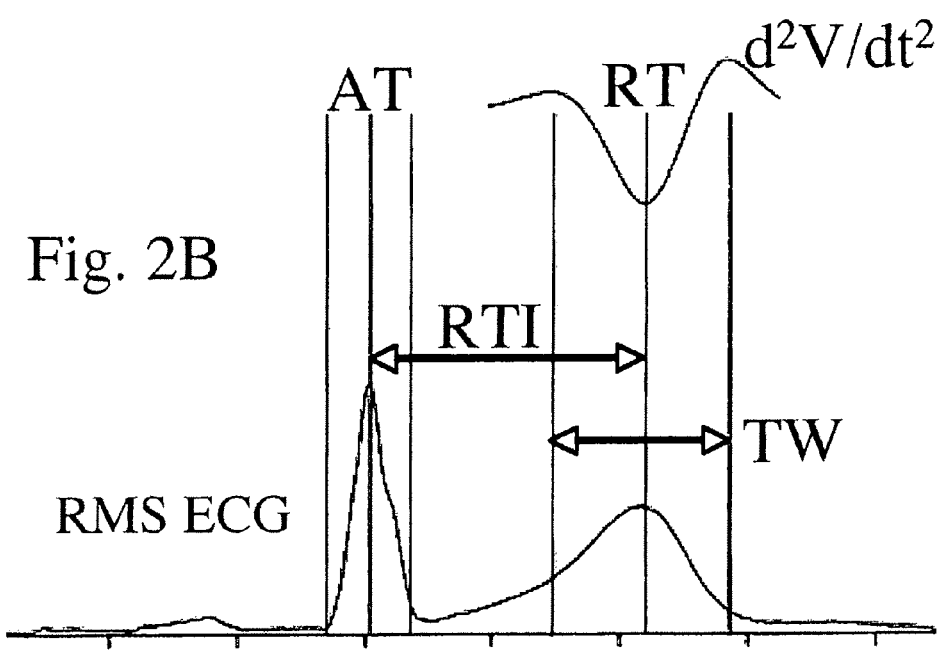

FIG. 2B illustrates an RMS ECG magnitude function derived in accordance with one embodiment of the present disclosure, including fiducial marks delineating the mean activation time (AT), mean repolarization time (RT), T-wave width (TW), the mean repolarization interval (RTI), and the QT interval. FIG. 2A illustrates the superimposed signals from the 12-leads of a standard clinical ECG. In the embodiment illustrated in FIG. 2A and FIG. 2B, the ECG generated by the sensor is a standard 12-lead clinical ECG, i.e. the measurement of the RMS variable is adapted to the standard 12-lead clinical ECG that is routinely performed in medical centers worldwide.

The RMS ECG magnitude function illustrated in FIG. 2A may be computed using a mathematical formula given by:

$$E_{RMS}(t) = \sqrt{\frac{1}{N}\sum e_i^2(t)} \quad (1)$$

where $E_{RMS}(t)$ represents the RMS magnitude function at a time t; and $e_i(t)$ represents the i-th electrocardiographic signal recorded at the time t.

Given a set of N, simultaneously recorded electrocardiographic signals, $\{e_i(t)\}$, for time t within a time interval, the RMS of these signals may be calculated using equation (1) above. The RMS magnitude function may be calculated from as few as two electrocardiographic leads, as used in 24 hour Holter recordings, or from standard 12 leads used in standard clinical ECGs. The RMS signal may further be calculated from hundreds of body surface ECGs. Furthermore, the RMS magnitude function maybe calculated from individually recorded beats, or from time-aligned and signal averaged beats.

The inflection points used to delineate QRS and T onsets and offsets may be substantially invariant to the number and location of the ECG leads. Baseline wander from individual ECGs must be removed, prior to the calculation of the RMS, typically by subtracting the line between P-R or T-P segments in adjacent beats. Without this baseline wander removal step, the RMS signal will be distorted, and the inflection points delineating QRS and T wave peaks, onsets and offsets will be perturbed.

In order to quantify the T onset, peak and offset times, i.e. the inflection points, a least mean squared error parabolic fit estimate of the RMS ECG may be performed, although other mathematical methods may also be used to quantify desired inflection points. This function may be implemented by centering a parabolic segment at each sample of the digital signal, $E_{RMS}(i\Delta t)$, where $\Delta t$ represents the digital sampling interval, and calculating the second derivative function, $E''_{RMS}(i)$, which enhances the delineating inflection points.

In this method, the second derivative function, $E''_{RMS}(i)$ is given by:

$$E''_{RMS}(i) = A\alpha + B\beta$$

where $$\alpha = E(i) + \sum_{j=1}^{M}[E(i+j) + E(i-j)],$$

$$\beta = \sum_{j=1}^{M} j^2[E(i+j) + E(i-j)],$$

$$S1 = 2M + 1,$$

$$S2 = M(M+1)(2M+1)/3,$$

$$S4 = M(M+1)(2M+1)(3M^2 + 3M - 1)/15,$$

$$D = S1 \cdot S4 - S2^2,$$

$$A = -S2/D,$$

$$B = S1/D,$$

and $2M\Delta t$ is defined as the "filter width", which for human T waves may be set at about 60 milliseconds for normal use or as high as 180 for excessively noisy signals.

FIG. 2B shows both $E_{RMS}(t)$ and $E''_{RMS}(t)$ superimposed over the T wave. It is seen from FIG. 2B that the minimum of the estimated derivative identifies the RMS T-peak, and that the two local maxima of the derivative on either side of the minimum identifies the inflection points of T onset and offset for the beat, respectively. The T width or TW is width of the T wave as defined by the interval between T onset and offset times. There may be some flexibility in selecting M, which may be increased to provide filtering for excessively noisy signals, although at the expense of widening the overall T width.

The QRS onsets and offsets may be identified more simply by threshold approaches. The RMS R peak time may be detected by finding the time of the maximum $E_{RMS}(t)$. When relatively low sampling rates are used (sampling intervals greater than about 4 milliseconds), the 2nd derivative extrema peaks may be interpolated between sampling intervals.

For each beat analyzed by the method described above, the following measurements may be made: 1) the RMS RT interval between R & T Peaks, which provides an estimate of the mean ventricular action potential duration; 2) the RMS QT interval between $Q_{onset}$ & $T_{end}$, which may be comparable to standard QT interval measurements; and 3) the RMS TW interval between $T_{onset}$ & $T_{end}$, which may provide an estimate of the dispersion of action potential downstroke times. The experimental observation that times of R and T peaks in the RMS ECG correspond to mean ventricular depolarization and repolarization times, respectively, may provide a sound electrophysiologic basis for these measurements.

Further, in conjunction with the preceding RR interval (cycle length) or, in the case of averaged beats, the mean cycle length of the beats, one may construct RMS QT:RR and RT:RR regression functions that provide a means to assess rate dependency of the heart. While the RMS signals that are obtained by using different leads may have different morphologies and amplitudes, the inflection points of QRS and T wave onsets, offsets and peaks are largely invariant.

Study of Drug-Induced Change in Cardiac Repolarization

In one study, drug-induced change in cardiac repolarization was evaluated by making RMS-TW measurements in accordance with the above description. The results were compared with QT duration measurements. Healthy volunteers were screened for inclusion in this study. Subjects with QTc (QT interval with correction)>410 msec, HR (heart rate)<50 BPM (beats per minute) or reduced serum potassium or magnesium were excluded. Thirty-nine subjects were enrolled and gave informed consent to undergo a 3-day study in a clinical research unit. On day 0, subjects were monitored without therapy. On day 1 all subjects received sotalol, 160 mg, orally at 8 AM while fasting. The protocol was repeated on day 2 with a sotalol dose of 320 mg. Only 22 of the original 39 subjects received the higher sotalol dose on day 3. On each day sixteen 12-lead ECGs were obtained immediately prior to the time of dosing and at 1, 1.5, 2, 2.5, 3, 3.5, 4, 4.5, 5, 6, 8, 10, 13, 16 and 22.5 hours after dosing with an Eli 200 electrocardiograph. A 12-lead, 24-hour Holter monitor was recorded on each of the three days from the same dual-snap electrode positions used for ECG recording. Only 1600 of the total of 3000 12-lead ECGs were available for this analysis due to loss of the remaining ECG files. The missing ECGs were replaced by ECGs extracted from the H-12 data stream. The extracted ECGs were analyzed by the same methods as the original 12-lead ECGs.

Measurement of RR and QT on ECG

Electrocardiographic RR and QT were determined using a system developed by Covance Cardiac Safety Services, Reno, Nev. Three consecutive beats during a period of rate stability in lead II were used to measure an average QT. An average RR interval was calculated using the cycles preceding each of the measured beats. When lead II was not adequate for measurement, lead V2 or V5, in descending priority, was used. The ECGs were then presented to a cardiologist in a computerized viewing system for adjustment of annotations at 1 msec resolution. The end of the T-wave was preferentially measured at the time of last voltage change, or, when necessary, at the intersection with the isoelectric baseline of a tangent to the most rapidly changing segment of the last limb of the T wave. The QT interval was corrected for heart rate using Fridericia formula. Standard and specialized ECG intervals were measured on ECGs obtained at baseline and at $T_{max}$ (2.5 hours after drug administration).

Measurements of RMS-RT, RMS-TW, and RMS-QT on ECG and Holter

The root-mean-square (RMS) value of the ECG waveform was calculated from two limb leads and all 6 precordial leads of both the standard 12-lead ECG and the 12-lead Holter, using an algorithm developed by Robert Lux (University of Utah). The RMS recovery time (RMS-RT) was measured from the QRS onset to the time of the peak of the RMS T wave.

The algorithm also measured RMS T-wave width (RMS-TW) from onset of the RMS T wave (the peak of the second time derivative during the transition from the ST segment to the T wave) to T-offset (the second positive peak of the $2^{nd}$ derivative at the transition from T wave to baseline). The RMS-QT was measured from the QRS onset to the time of RMS T-offset. The algorithm automatically scanned the ECG and Holter data to exclude ectopic beats and regions of excessive noise. For the 12-lead ECG analysis, all beats during the 10-second recording were used in the calculation. For the Holter analysis, data averaged over five minutes epochs were used in the calculation each variable.

ECG Data at Tmax

FIG. 3A is a table displaying the percent change over the same time point during the baseline day of standard and specialized intervals measured on 10-second, 12-lead ECGs at Tmax. Tmax was identified in each individual subject-day by examination of the RMS-RT curve. In those instances in which a clear Tmax could not be identified, the population's mean value was used. The changes in RMS-TW were considerably and statistically significantly greater than the changes in QTcF. The change for day 3 was greater than that for day 2 for all measures, but the difference between the two days was greater for RMS-TW.

Holter Data

FIGS. 4A-4G illustrate Holter ECG data for the three RMS—derived repolarization variables RT, QT, and RMS-TW along with RR in an individual subject. In particular, FIGS. 4A, 4B, 4C and 4D show continuous measures of heart rate and the three repolarization variables RT, QT, and TW at baseline (day 0) and on the two days that sotalol was administered at 160 mg (day 1) and 320 mg (day 2). During the baseline day (day 0) heart rate and the repolarization intervals were relatively stable until after bedtime, when RR interval increased. RMS-QT also increased, but RMS-TW remained unchanged. On both day 1 and day 2, in addition to the nighttime increases, all three variables were seen to increase after drug administration.

Figure 4A:
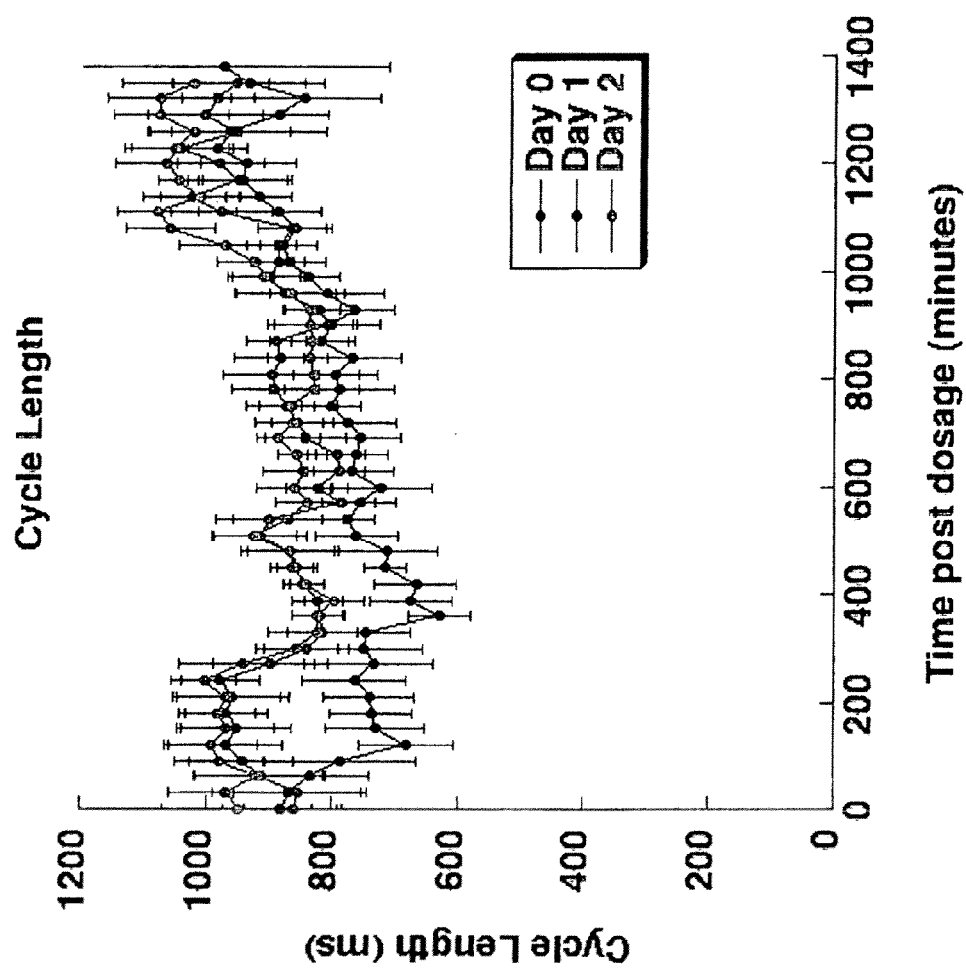
FIGS. 4A-4G illustrate Holter ECG data for the three RMS-derived repolarization variables RT, QT, and RMS-TW (T wave width) along with RR in an individual subject who received sotalol. Also shown are changes in these variables.
Figure 4B:
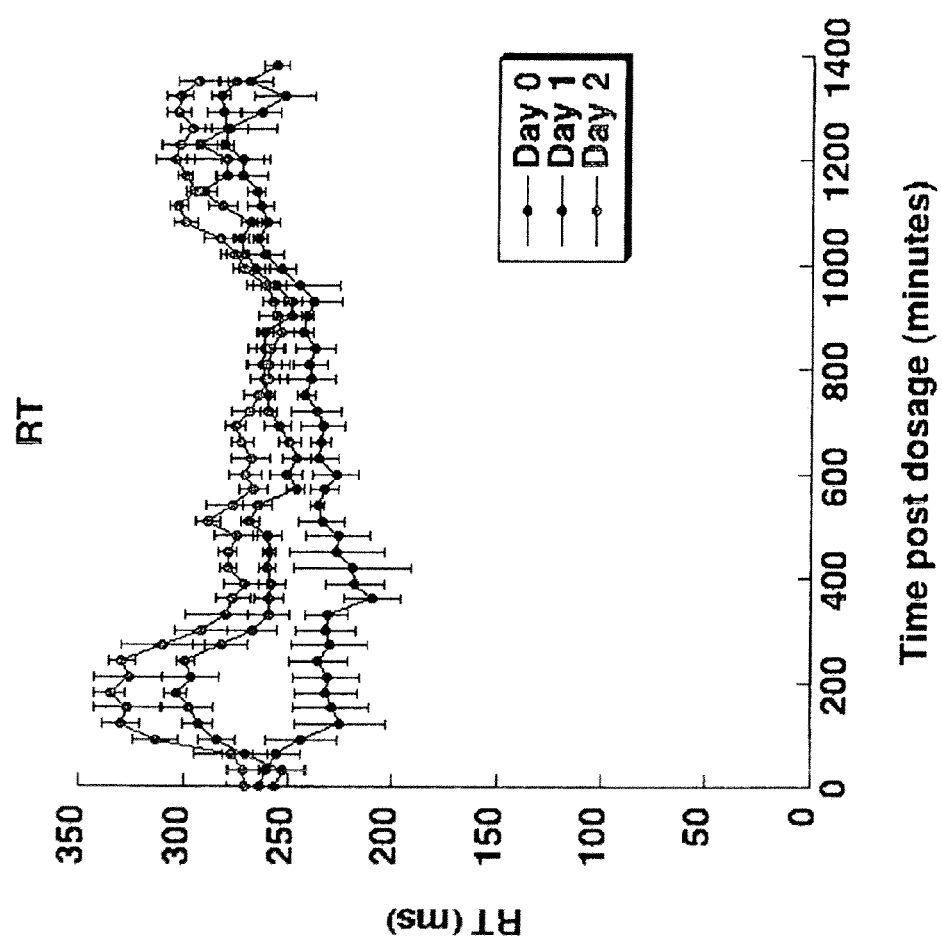
Figure 4C:
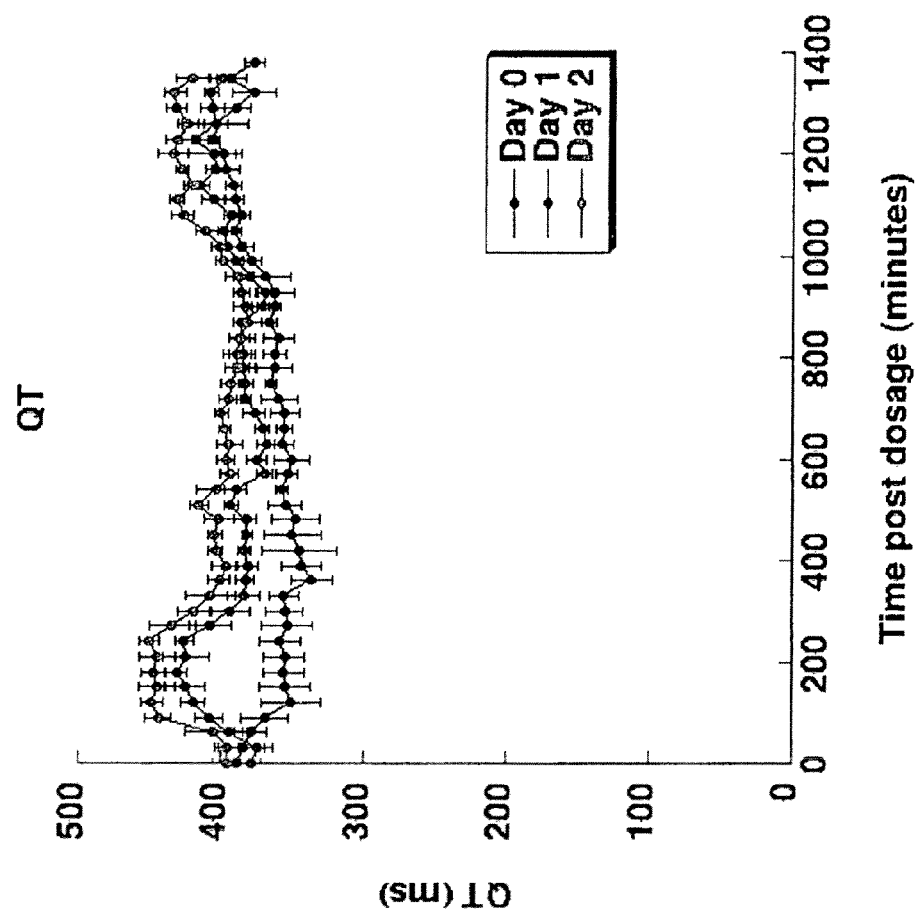
Figure 4D:
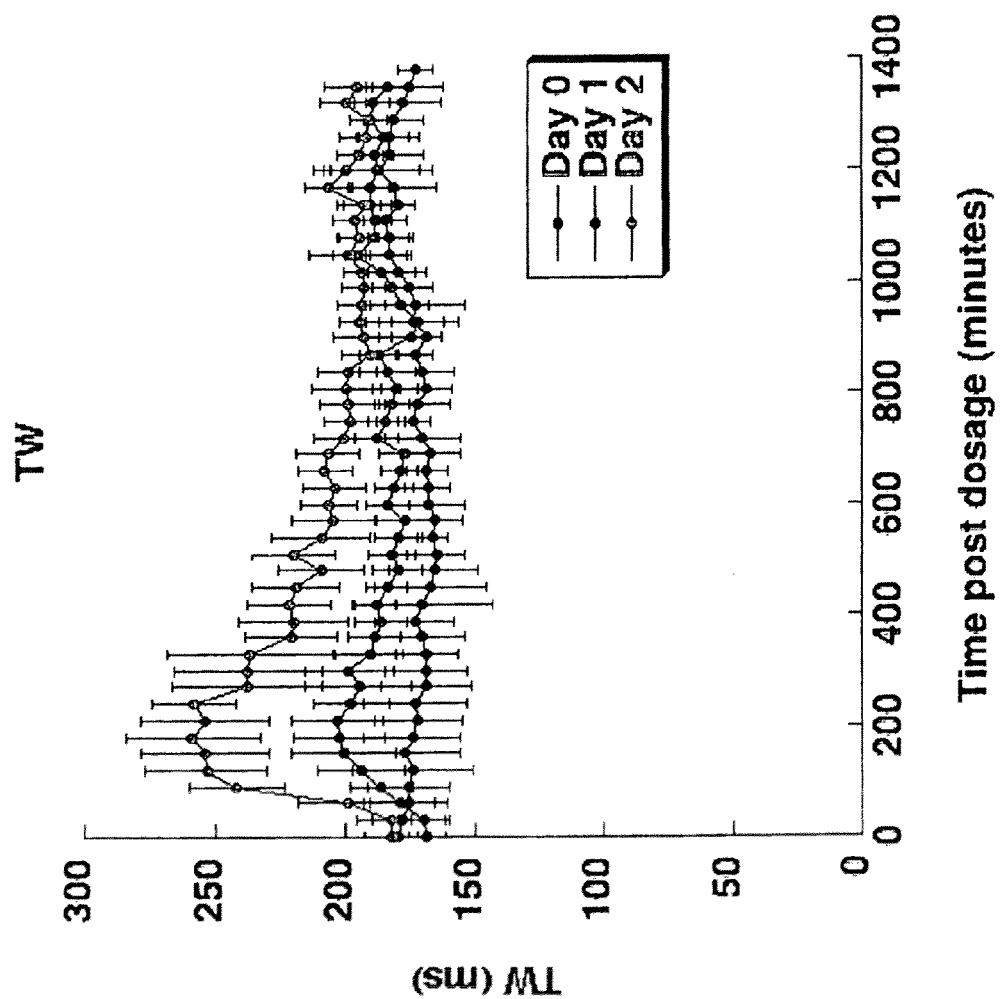
Figure 4E:
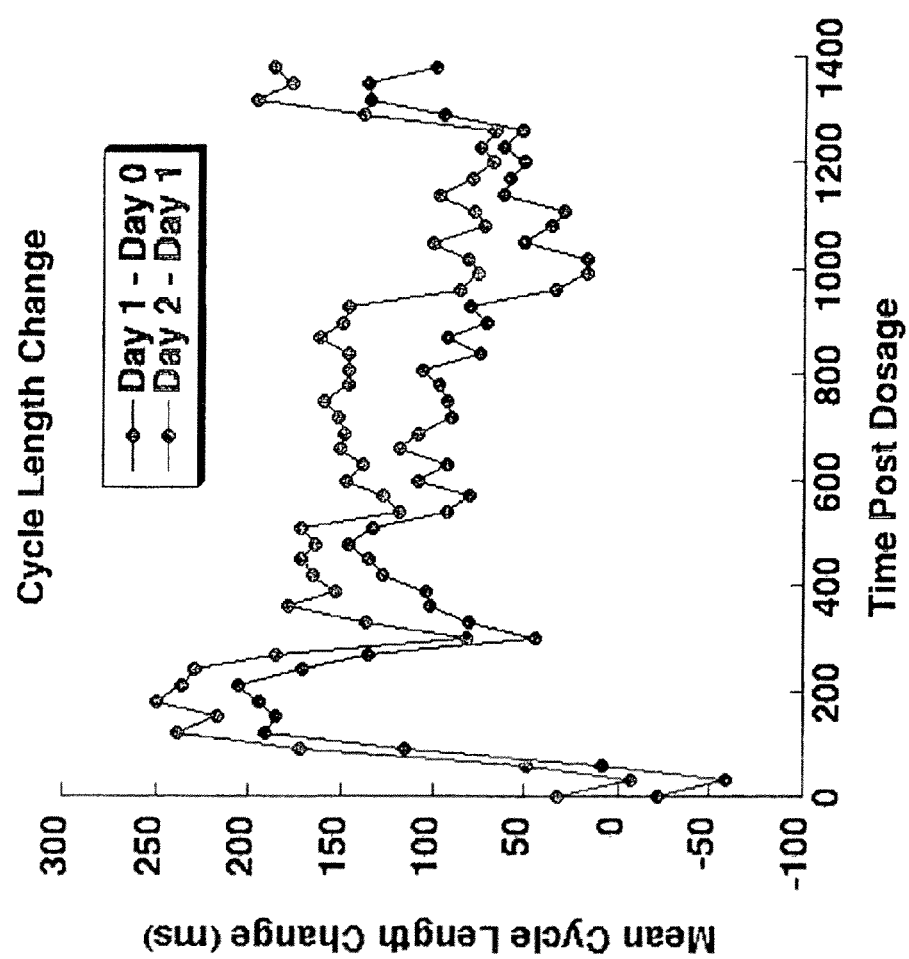
Figure 4F:
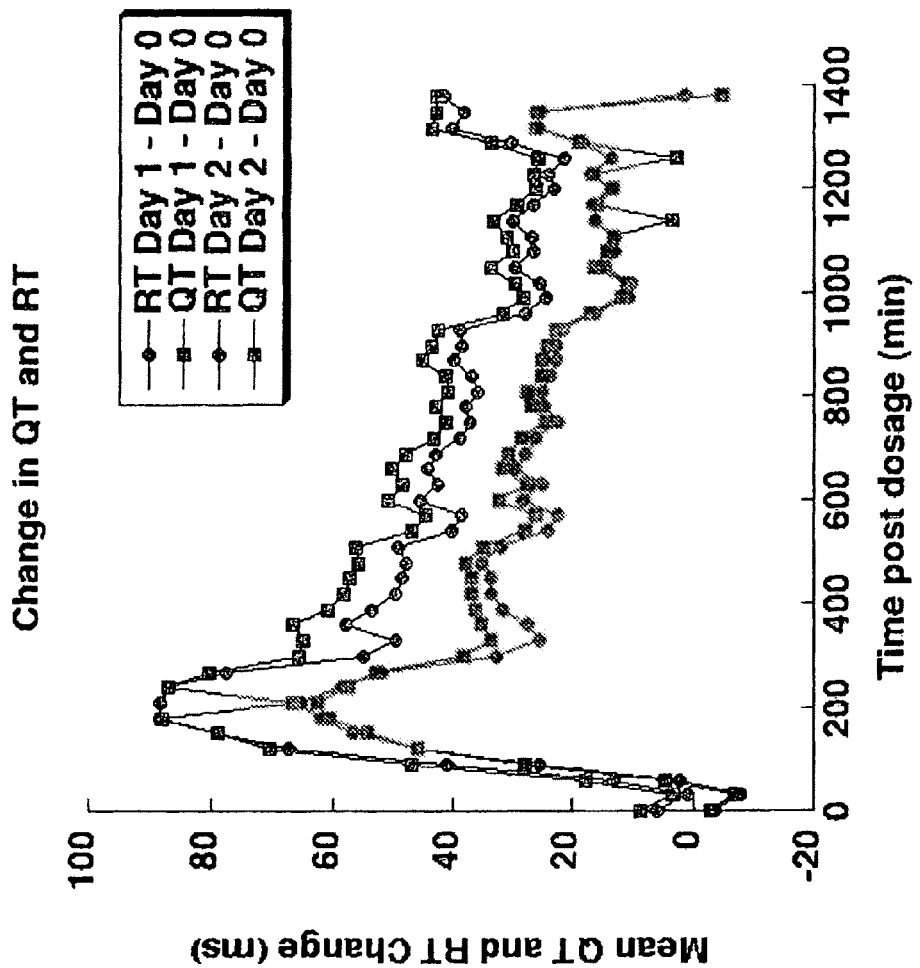
Figure 4G:
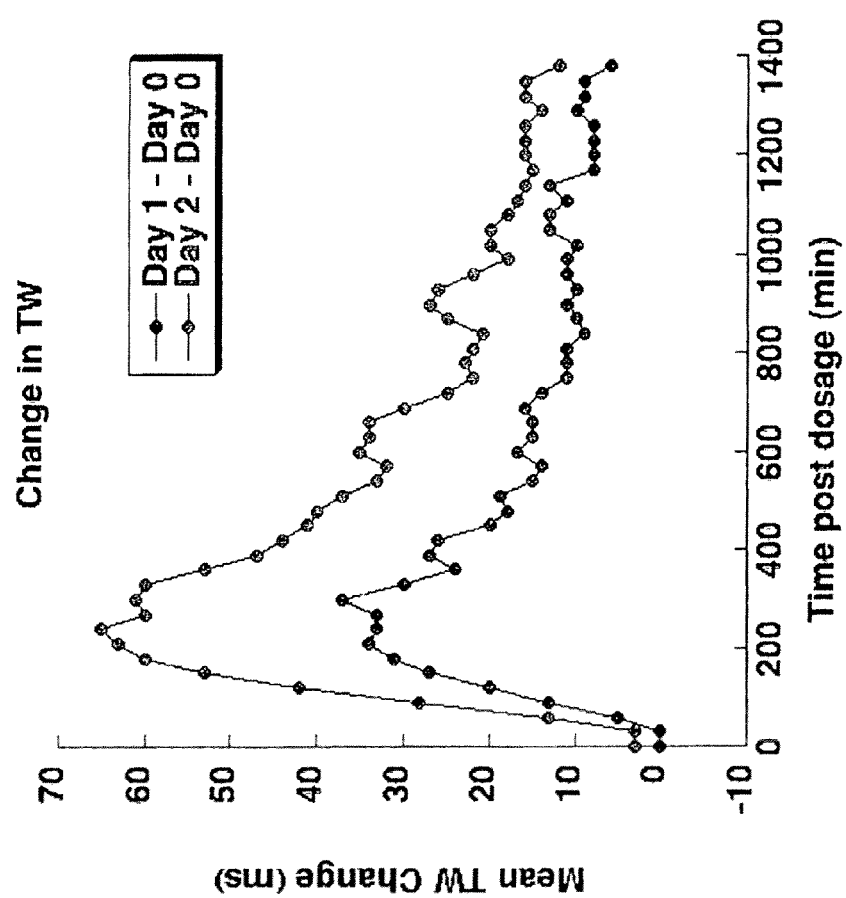

FIG. 4E, 4F and 4G show changes in RR, RT, QT and between each of the on-drug days and the control day. In addition, the change in RMS-TW persisted longer than that of the other two variables. These differences are exaggerated in day 2 compared with day 1.

Heart-rate Dependency

Figure 5:
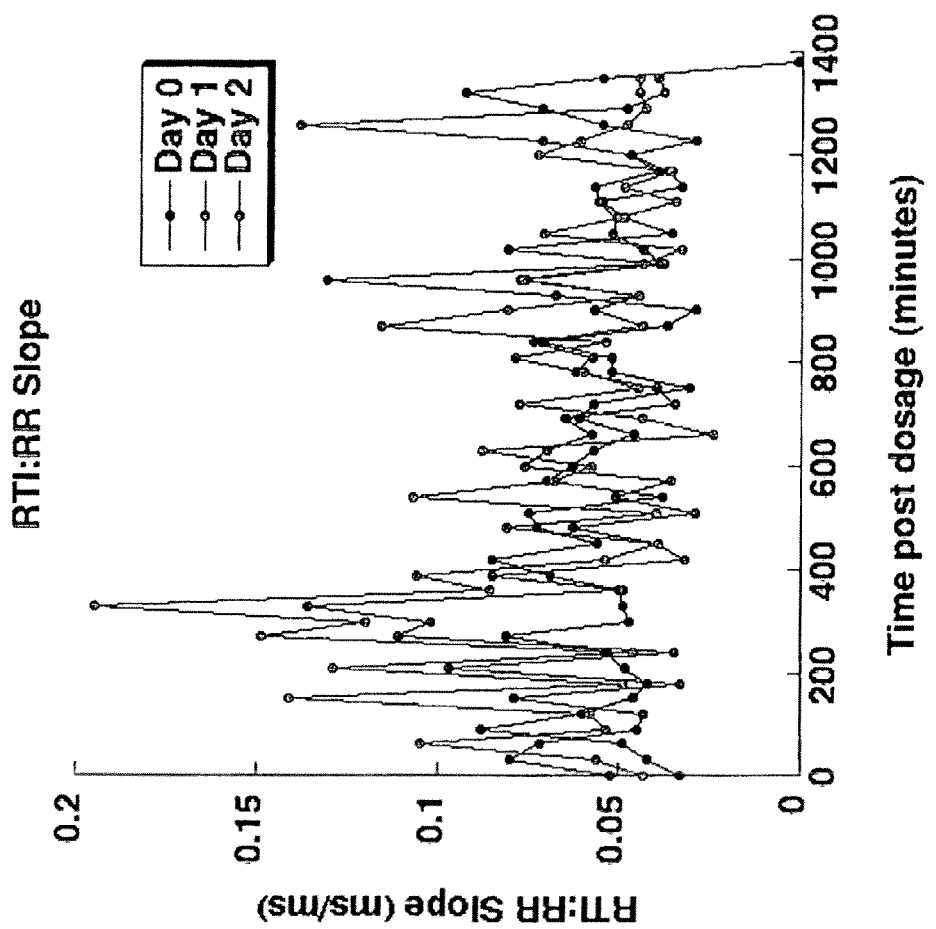
FIG. 5 shows the RT:RR slope over time in a single subject.

As shown in FIG. 4D discussed above, RMS-TW did not change with the nighttime decrease in heart rate. FIG. 5 shows the RT:RR slope over time for all three days in a single subject. In particular, the figure shows the 30-minute slope averages over time. At baseline (shown in FIG. 5), the positive slope relationship for RMS-RT is shown to transiently increase during mealtimes and to decrease during sleep. Under the influence of sotalol a large rise in slope occurs. On all three days the RMS-TW RR slope is nearly flat.

As shown in the table in FIG. 3B, which displays data from the previously described analysis in 13 subjects who received two doses of sotalol after a baseline day, the slope of RMS-TW on RR-interval was negligible and an order of magnitude smaller than that of QT.

RMS T-wave Onset and Offset

Figure 6:
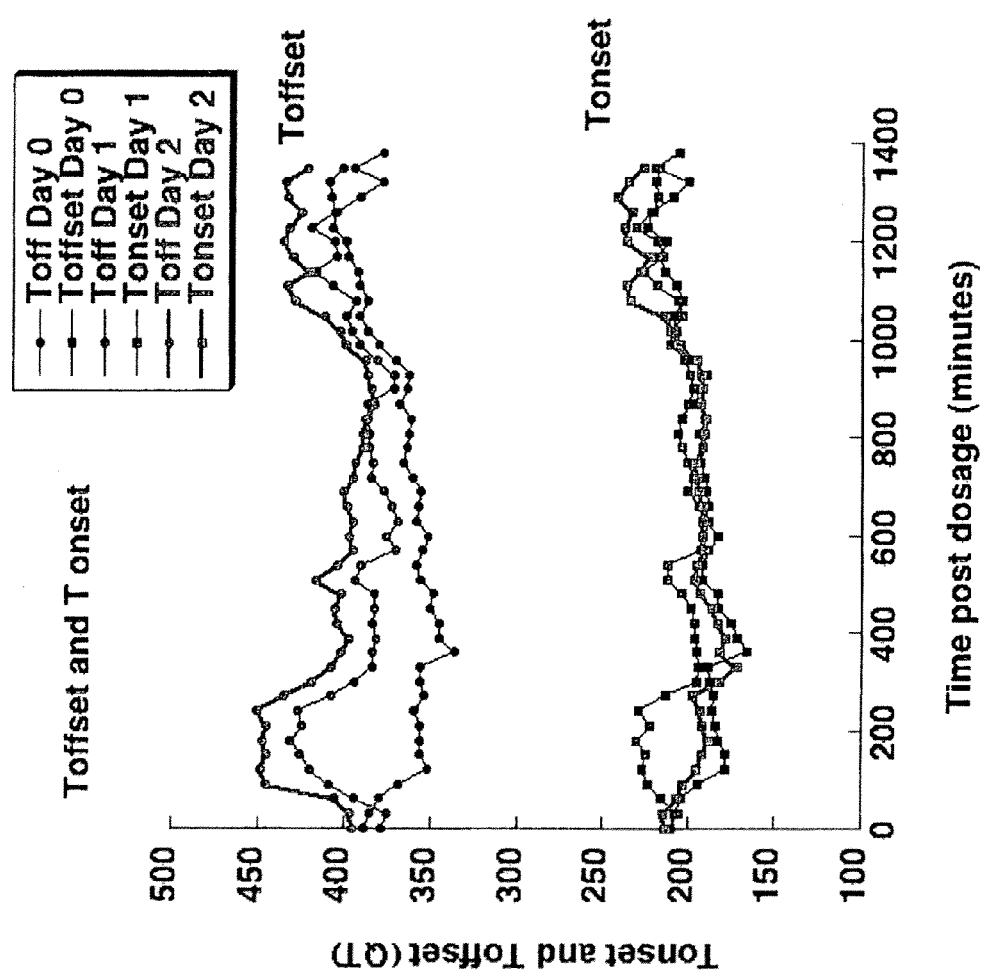
FIG. 6 illustrates the time after Q onset of RMS-T wave onset and offset in an individual subject who received sotalol.

FIG. 6 illustrates the time after Q onset of RMS-T wave onset and offset in an individual subject.

In some subjects, the RMS-TW offset was delayed with respect to the onset of the QRS complex during therapy with sotalol, as illustrated in FIGS. 7A and 7B. FIG. 7A was obtained during the baseline day at a time corresponding to Tmax in a single subject. FIG. 7B was obtained at $T_{max}$ following administration of 160 mg of sotalol. The heart rate was similar during both recordings. RMS-TW increased during therapy by 70 msec, substantially due to earlier T-wave onset. As illustrated in FIGS. 7A and 7B, in some subjects the increase in RMS-TW resulted from isolated early onset. In other words, repolarization heterogeneity increased without lengthening of the total duration of repolarization.

The study described above showed that RMS-TW derived from standard 12-lead electrocardiographic data is a more sensitive indicator than QTcF of sotalol-induced change in repolarization in humans. Both QTcF and RMS-TW were found to be more informative when they are based upon a large number of measurements from a Holter data stream, as compared to a limited number of measurements from a 10-second ECG. In addition, RMS-TW was less rate dependent, i.e. was nearly independent of heart rate. Without rate correction, RMS-TW outperformed the other rate-corrected measures. Finally, RMS-TW was more sensitive to beat-to-beat instability induced by sotalol.

The RMS method of ECG waveform analysis, described above, allowed data to be collected from multiple beats and leads to form a single analyzable QRST waveform. The techniques used to derive informative data from these waveforms were based upon observed correlations between cellular, whole organ and body surface electrophysiologic recordings. RMS-TW may be superior to QT duration measurements, at least in part because RMS-TW is not a measure of the duration of repolarization per se, but rather an indicator of the range of repolarization times within the ventricles. Accordingly, an intervention which increases regional repolarization time throughout the myocardium by a fixed quantity may not change RMS-TW, while an intervention which increases repolarization by a fixed proportion of time, or one which had varying regional effects, would be expected to change RMS-TW. In the case of sotalol, drug-induced QT lengthening may not be as prominent an effect as the drug-related increase in heterogeneity of regional repolarization duration. Regional heterogeneity of repolarization may be a more powerful risk factor for ventricular arrhythmias than mere prolongation of repolarization.

In the above-described study, earlier RMS-TW onset was observed during treatment with sotalol, in addition to the expected delay in RMS-TW offset.

In sum, fiducial marks from a simple RMS signal, calculated from a wide variety and range of electrocardiographic signals may provide, on a beat-to-beat basis, estimates of a) the mean ventricular depolarization time, b) the mean ventricular repolarization time, c) the mean ventricular action potential duration, and d) the ranges of both depolarization and repolarization times. The timing of the inflection points in the RMS ECG was not particularly sensitive to the number and location of ECG leads used for its calculation. Preferably, a minimum of at least two independent signals are used for RMS construction.

While certain embodiments have been described of systems and methods of RMS electrocardiography, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method comprising:
recording a plurality of electrocardiographic signals of a subject to generate at least one ECG (electrocardiogram) of the subject;
computing an RMS (root-mean-square) magnitude function from the recorded electrocardiographic signals; and
computing estimates of one or more RMS variables that contain information about a cardiac condition of the subject with fiducial marks from the RMS magnitude function providing, on a beat by beat basis, estimates of: a mean ventricular depolarization time, a mean ventricular repolarization time, a mean ventricular action potential duration, and a range of the depolarization time and the repolarization time;
wherein a mathermatical formulation of the RMS magnitude function comprises:

$$E_{RMS}(t) = \sqrt{\frac{1}{N} \sum e_i^2(t)}$$

where $E_{RMS}(t)$ represents the RMS magnitude function at a time t; and $e_i(t)$ represents the i-th eletrocardiographic signal recorded at the time t.

2. The method of claim 1,
wherein at least one of the RMS variable is substantially independent of the subject's heart rate; and wherein the RMS variables comprise an RMS T-wave width of the ECG.

3. The method of claim 1, wherein the cardiac condition comprises at least one of:
ventricular repolarization of the subject;
an average cardiac repolarization time of the subject, and
a duration of ventricular action potential of the subject.

4. The method of claim 1, wherein the RMS variable comprises at least one of:
an RMS RT recovery time of the ECG; and
an RMS QT interval of the ECG.

5. The method of claim 1, wherein the act of recording the electrocardiographic signals of the subject comprises coupling a plurality of ECG leads to the subject to receive the electrocardiographic signals from the subject.

6. The method of claim 5, wherein the RMS magnitude function includes a plurality of inflection points that are substantially invariant to a number and a location of the ECG leads.

7. The method of claim 1, wherein the acts of computing the RMS magnitude function and computing estimates of the RMS variables comprise using a processor.

* * * * *